United States Patent
Schmid et al.

(10) Patent No.: US 11,877,813 B2
(45) Date of Patent: Jan. 23, 2024

(54) TROCAR SIMULATION

(71) Applicant: Cilag GmbH International, Zug (CH)

(72) Inventors: Katherine J. Schmid, Loveland, OH (US); Eric W. Thompson, Pleasant Plain, OH (US); Cara Shapiro, Milford, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 16/743,771

(22) Filed: Jan. 15, 2020

(65) Prior Publication Data

US 2020/0146760 A1    May 14, 2020

Related U.S. Application Data

(62) Division of application No. 15/380,490, filed on Dec. 15, 2016, now Pat. No. 10,568,706.

(51) Int. Cl.
*A61B 34/30* (2016.01)
*A61B 17/34* (2006.01)
(Continued)

(52) U.S. Cl.
CPC .......... *A61B 34/30* (2016.02); *A61B 17/3423* (2013.01); *A61B 34/10* (2016.02); *A61B 34/70* (2016.02); *A61B 34/71* (2016.02); *A61B 90/361* (2016.02); *A61B 90/50* (2016.02); *A61B 17/3462* (2013.01); *A61B 2017/347* (2013.01);
(Continued)

(58) Field of Classification Search
CPC ...... A61B 34/00; A61B 17/3462; A61B 17/00
See application file for complete search history.

(56) References Cited

U.S. PATENT DOCUMENTS 5,441,042 A * 8/1995 Putman .................... B25J 9/042
                                              600/102
6,123,689 A * 9/2000 To ......................... A61B 17/3462
                                              604/167.01
(Continued)

FOREIGN PATENT DOCUMENTS

| WO | 2014151621 A1 | 9/2014 |
| WO | 2015167808 A1 | 11/2015 |
| WO | 2016168226 A1 | 10/2016 |

OTHER PUBLICATIONS

International Search Report and Written Opinion for International App. No. PCT/IB2017/057299 dated Feb. 5, 2018 (12 pages).

*Primary Examiner* — Lynsey C Eiseman
(74) *Attorney, Agent, or Firm* — Mintz Levin Cohn Ferris Glovsky and Popeo, P.C.

(57) ABSTRACT

Methods and devices are provided for supporting an elongate shaft on a surgical tool during robotic surgery. For example, a tool holder is provided with an elongate carrier arm configured to couple to a distal end of a surgical robotic arm. The tool holder has a housing that is removably mounted on the carrier arm and that is configured to be positioned adjacent to a tissue surface without extending into tissue. The tool holder thus simulates a trocar. The housing has an opening formed therethrough for receiving an elongate shaft of a surgical tool, and the opening has an inner diameter that is configured to dynamically adjust in size to adapt to and resist movement of elongate shafts of varying diameters inserted therethrough.

10 Claims, 3 Drawing Sheets

(51) Int. Cl.
  *A61B 34/00* (2016.01)
  *A61B 34/10* (2016.01)
  *A61B 90/00* (2016.01)
  *A61B 90/50* (2016.01)

(52) U.S. Cl.
  CPC ............ *A61B 2017/3409* (2013.01); *A61B 2017/3492* (2013.01); *A61B 2034/104* (2016.02)

(56) References Cited

U.S. PATENT DOCUMENTS

| | | |
|---|---|---|
| 6,705,474 B1 | 3/2004 | Buczek |
| 6,726,699 B1 | 4/2004 | Wright et al. |
| 7,988,672 B2 * | 8/2011 | Heinrich ............ A61B 17/3439 604/167.06 |
| 8,114,345 B2 | 2/2012 | Dlugos, Jr. et al. |
| 2007/0089557 A1 | 4/2007 | Solomon et al. |
| 2010/0010446 A1 * | 1/2010 | Schweitzer ........ A61B 17/3498 604/167.01 |
| 2010/0286706 A1 * | 11/2010 | Judson ............... A61B 17/3462 606/108 |
| 2012/0168587 A1 * | 7/2012 | Karsak .................. A61B 90/39 248/291.1 |
| 2014/0378996 A1 | 12/2014 | Ferzli |
| 2016/0151120 A1 | 6/2016 | Kostrzewski et al. |
| 2017/0238829 A1 * | 8/2017 | Parker .................. A61B 5/6852 |
| 2017/0325799 A1 * | 11/2017 | Wixey .................. A61B 34/37 |
| 2018/0168743 A1 | 6/2018 | Schmid et al. |

\* cited by examiner

TROCAR SIMULATION

CROSS REFERENCE TO RELATED APPLICATIONS

This application is a divisional of U.S. patent application Ser. No. 15/380,490 filed Dec. 15, 2016, entitled "Trocar Simulation," which is hereby incorporated by reference in its entirety.

FIELD

Methods and devices are provided for supporting an elongate shaft on a surgical tool during robotic surgery.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity, and sensitivity of endoscopic tools has been found to be an impediment in the increased the use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

While significant advances have been made in the field of robotic surgery, there remains a need for improved methods, systems, and devices for use in robotic surgery.

SUMMARY

Various surgical tools and methods are provided for supporting an elongate shaft on a surgical tool during robotic surgery. In one aspect, a tool holder is provided that includes an elongate carrier arm configured to couple to a distal end of a surgical robotic arm. The tool holder has a removable housing mounted on the carrier arm. The housing has an opening formed therethrough for receiving an elongate shaft of a surgical tool, and it is configured to be positioned adjacent to a tissue surface without extending into tissue. The opening has an inner diameter that is configured to dynamically adjust in size to adapt to and resist movement of elongate shafts of varying diameters inserted therethrough.

The tool holder can vary in numerous ways. For example, the housing can be mounted on a distal end of the carrier arm, and the proximal end of the carrier arm can include a tool driver with a plurality of motors for driving a tool. The opening can include at least one engagement feature disposed therein that is configured to adjust the size of the inner diameter of the opening. The inner diameter can also be configured to automatically dynamically adjust in size during insertion of an elongate shaft therethrough. In another example, the opening can include a variety of features, such as ribs, spring-biased centering balls, spring-biased arms, semi-segmented balloons, and an elastomeric squeeze fit material for adjusting a size of the inner diameter of the opening. The housing can be ring-shaped and mounted on a distal-most end of the carrier arm.

In another aspect, a surgical system is provided that includes a surgical tool with a housing and an elongate shaft extending from the housing with an end effector at a distal end. The system has a robotic arm with a tool driver on a distal end thereof. The tool driver includes a plurality of motors configured to couple to the housing on the tool for driving the tool. The system also has a tool holder with an opening formed therethrough to receive the elongate shaft when the housing is coupled to the tool driver, and it is configured to be positioned adjacent to a tissue surface without extending into tissue. The opening includes at least one engagement feature that is configured to alter a diameter of the opening such that the opening can receive and engage elongate shafts of varying diameters.

The system can vary in numerous ways. For example, the at least one engagement feature can include at least one biasing member that is configured to bias the elongate shaft toward a center of the opening. In certain aspects, the at least one engagement feature can include at least one of ribs, spring-biased centering balls, spring-biased arms, semi-segmented balloons, and an elastomeric squeeze fit material. The elongate shaft can have a longitudinal axis and the tool holder can be configured to resist a change in an angular orientation of the elongate shaft relative to the longitudinal axis. In another example, the tool holder can include a ring having the opening in a center thereof.

In another aspect, a surgical method is provided that includes inserting an elongate shaft of a surgical tool into an opening of a tool holder mount on a distal end of a surgical robotic arm. The tool holder is positioned adjacent to a tissue surface without extending into tissue. The opening dynamically adapts in size to have an inner diameter that substantially corresponds to an outer diameter of the elongate shaft such that the tool holder resists angular forces applied to the elongate shaft to minimize a bending load applied to the shaft.

The surgical method can vary in numerous ways. For example, the opening can have at least one biasing member that biases the elongate shaft toward a center of the opening to resist angular forces applied to the elongate shaft. The at least one biasing member can include, for example, at least one of ribs, spring-biased centering balls, spring-biased arms, semi-segmented balloons, and an elastomeric squeeze fit material. The opening can include a plurality of spring-biased members that are biased toward a central axis of the opening to adjust a size of the inner diameter of the opening. The opening can also include at least one deformable member that deforms to adjust a size of the inner diameter of the opening. In another example, the tool holder can be mounted on a distal end of a carrier arm coupled to the distal end of the surgical robotic arm, and a housing of the surgical tool can be movably coupled to a tool driver mounted on a proximal portion of the carrier arm. The tool holder can also be positioned against an outer surface of a patient to mimic the function of a trocar.

BRIEF DESCRIPTION OF THE DRAWINGS

The invention will be more fully understood from the following detailed description taken in conjunction with the accompanying drawings, in which.

DETAILED DESCRIPTION

Figure 1:
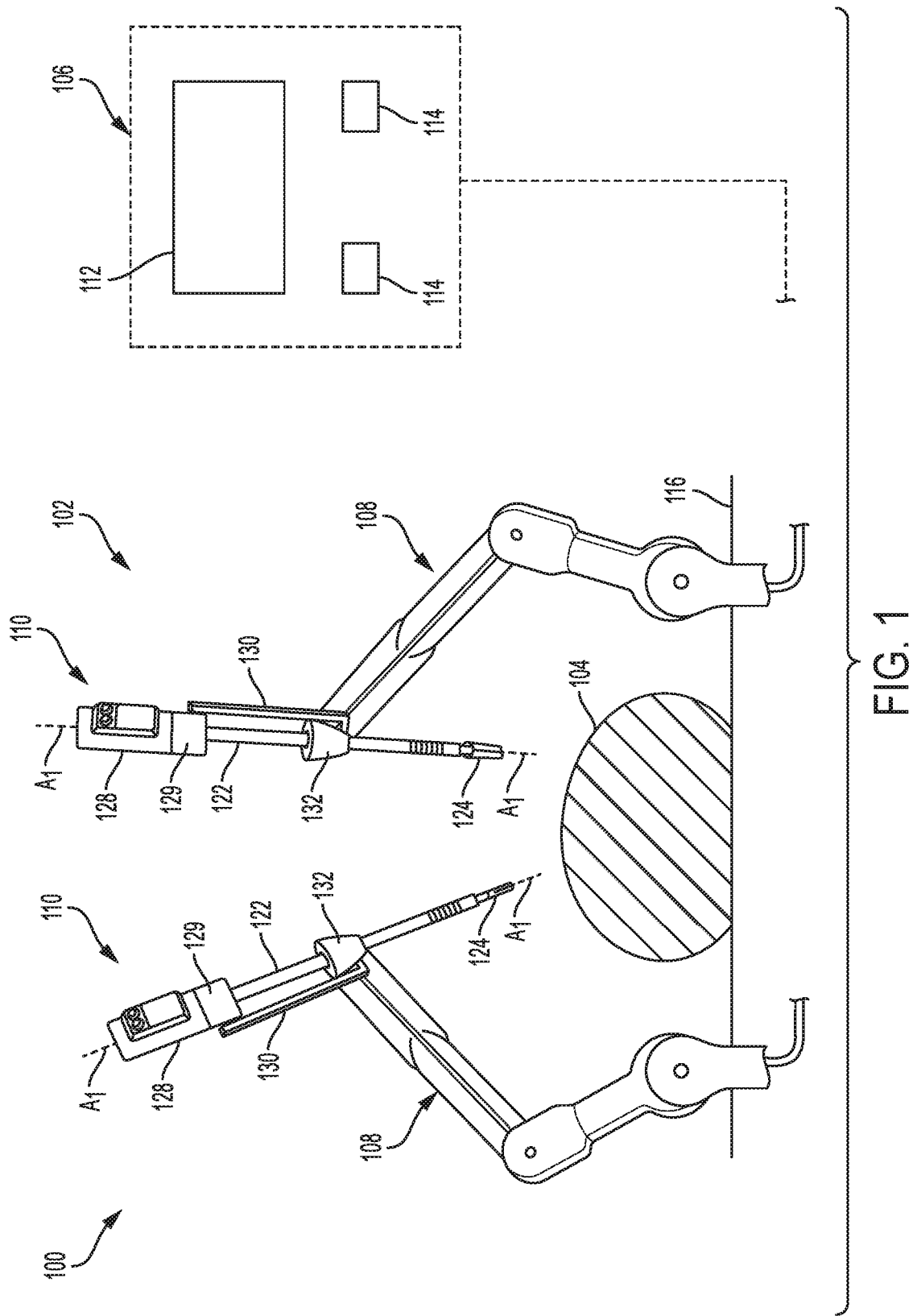
FIG. 1 is a perspective view of one embodiment of a surgical robotic system that includes a patient-side portion and a user-side portion.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various surgical tool holding devices and methods are provided in which many of the functions common to a surgical trocar, such as surgical tool support, are replaced by a tool holder. Robotic surgical tools generally have a housing and an elongate tool shaft extending from the housing with an end effector on a distal end thereof. The housing has a plurality of actuators for causing various functions of the end effector, such as rotation, articulation, clamping, firing, stapling, etc. Many surgical tools with elongate shafts benefit from additional support provided to the shaft by a trocar during surgical procedures to center the surgical tool and prevent or limit undesirable bending loads and/or forces from being applied to the shaft and/or the surgical tool. When a surgical tool is coupled to a robotic surgical system, additional bending loads may be applied at an engagement point between the surgical tool and the robotic surgical system. A trocar can help reduce the load and stabilize the tool. However, the use of a trocar may not be ideal in all situations, such as in thoracic cases. Additionally, a user may want to use a surgical tool without using a trocar, a user may want to use a smaller diameter tool that will not receive full support from a trocar, or a user may not want to insert a trocar abdominally into a patient. Furthermore, some robotic surgical systems may incorporate various sensing mechanisms to ensure a trocar is in place and will not operate without a trocar being sensed. Provided herein is thus a tool holder configured to receive an elongate shaft of a surgical tool in an opening therethrough. The opening is configured to dynamically adjust in size to adapt to and resist movement of elongate shafts of varying diameters inserted therethrough. The tool holder is configured to connect to robotic surgical system arms and to simulate a trocar.

FIG. 1 is a perspective view of one embodiment of a surgical robotic system 100 that includes a patient-side portion 102 that is positioned adjacent to a patient 104, and a user-side portion 106 that is located a distance from the patient, either in the same room and/or in a remote location. The patient-side portion 102 generally includes one or more robotic arms 108 and one or more surgical tools and/or tool assemblies 110 that are configured to releasably couple to a robotic arm 108. The user-side portion 106 generally includes a vision system 112 for viewing the patient 104 and/or surgical site, and a control system 114 for controlling the movement of the robotic arms 108 and each surgical tool 110 during a surgical procedure. A person skilled in the art will appreciate that the surgical robotic system can have a variety of configurations. One exemplary surgical robotic system is disclosed in WIPO Patent Publication No. WO2014/151621, filed on Mar. 13, 2014 and entitled "Hyperdexterous Surgical System," which is incorporated herein by reference in its entirety.

The surgical tool 110 includes an elongate shaft 122, an end effector 124, and a tool housing 128 coupled to a proximal end of the shaft 122. The end effector 124 is configured to move relative to the shaft 122, e.g., by pivoting, to position the end effector 124 at a desired location relative to a surgical site during use of the tool 110. The housing 128 includes various components (e.g., gears and/or actuators) configured to control the operation various features associated with the end effector 124 (e.g., any one or more of clamping, firing, rotation, articulation, energy delivery, etc.). In at least some embodiments, as in this illustrated embodiment, the surgical tool 110 is configured to releasably couple to a tool driver 129 mounted on a carrier 130 on a distal end of the robotic arm 108. The tool housing 128 can include coupling features configured to allow the releasable coupling of the tool 110 to the tool driver 129. The surgical tool 110 can have any of a variety of configurations. In general, the surgical tool can be configured to perform at least one surgical function and can include any of, for example, forceps, a grasper, a needle driver, scissors, an electrocautery tool that applies energy, a stapler, a clip applier, a suction tool, an irrigation tool, an imaging device (e.g., an endoscope or ultrasonic probe), etc. The surgical tool 110 in at least some embodiments is configured to apply energy (such as radiofrequency (RF) energy) to tissue, while in other embodiments the tool 110 is not configured to apply energy to tissue.

The shaft 122 can have any of a variety of configurations. In general, the shaft 122 is an elongate member extending distally from the housing 128 and having at least one inner lumen extending therethrough. The shaft 122 is fixed to the housing 128, but in other embodiment the shaft 122 can be releasably coupled to the housing 128 such that the shaft 122 can be interchangeable with other shafts. This may allow a single housing 128 to be adaptable to various shafts having different end effectors.

The control system 114 can have a variety of configurations and can be located adjacent to the patient (e.g., in the operating room), remote from the patient (e.g., in a separate control room), or distributed at two or more locations (e.g., the operating room and/or separate control room(s)). As an example of a distributed system, a dedicated system control console can be located in the operating room, and a separate console can be located in a remote location. The control system 114 can include components that enable a user to view a surgical site of the patient 104 being operated on by the patient-side portion 102 and/or to control one or more parts of the patient-side portion 102 (e.g., to perform a surgical procedure at the surgical site). In some embodiments, the control system 114 can also include one or more manually-operated input devices, such as a joystick, exoskeletal glove, a powered and gravity-compensated manipulator, or the like. The one or more input devices can control teleoperated motors which, in turn, control the movement of the surgical system, including the robotic arms 108 and surgical tools 110.

The patient-side portion 102 can have a variety of configurations. As illustrated in FIG. 1, the patient-side portion 102 can couple to an operating table 116. However, in other embodiments, the patient-side portion 102 can be mounted to a wall, to the ceiling, to the floor, or to other operating room equipment. Further, while the patient-side portion 102 is shown as including two robotic arms 108, more or fewer robotic arms 108 may be included. Furthermore, the patient-side portion 102 can include separate robotic arms 108 mounted in various positions, such as relative to the surgical table 116 (as shown in FIG. 1). Alternatively, the patient-side portion 102 can include a single assembly that includes one or more robotic arms 108 extending therefrom.

Figure 2:
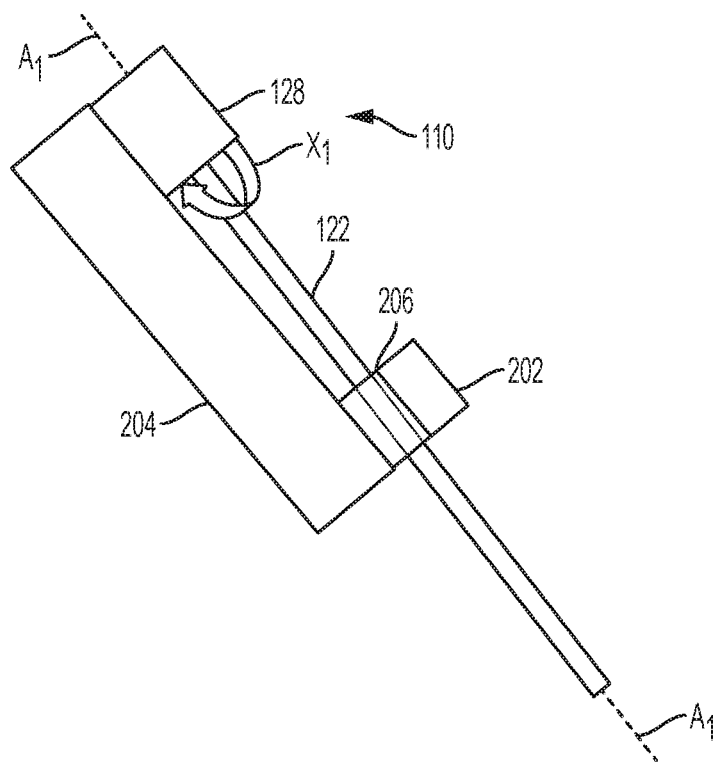
FIG. 2 is a perspective, partially-transparent view of the surgical tool of FIG. 1 in a robotic arm with a trocar simulation device.

As the surgical tool 110 is used during a surgical operation, various loads and/or forces are applied to the surgical tool because of movement of the surgical tool 110 and resistance encountered by other tools, equipment and/or tissue during the operation. While the surgical tool 110 can extend through a trocar (as shown in FIG. 1) to facilitate positioning within a body cavity, the surgical tool 110 can alternatively extend through a tool holder 202 coupled to a carrier 204 that attaches to a distal end of a robot arm (not shown), as illustrated in FIG. 2. The tool holder 202 can be configured to mimic a trocar without extending into tissue, and as shown has an opening 206 therethrough sized to receive the shaft 122 of the surgical tool 110. As illustrated by the arrow $X_1$ in FIG. 2, loads and/or forces encountered by the shaft 122 of the surgical tool 110 during use can cause the surgical tool 110 to angle away from a center or desired orientation, and the forces can apply undesired force to any engagement between the surgical tool 110 and any robotic surgical system to which it might be coupled, such as the tool driver 129 shown in FIG. 1. The tool holder 202 provides support to the surgical tool 110 to resist bending, shifting and/or angular movement of the shaft 122 by engaging the shaft 122 that extends through the opening 206 of the tool holder 202. The tool holder 202 is in the shape of a ring, but a variety of different shapes can be used, such as rectangular, oval, etc. The tool holder 202 can be removably mounted on a carrier 204 on a robotic arm in the same way that the trocar or trocar support 132 is mounted on the carrier 130 in FIG. 1. A user can thus selectively utilize either a trocar or a tool holder, as may be desired.

Figure 3:
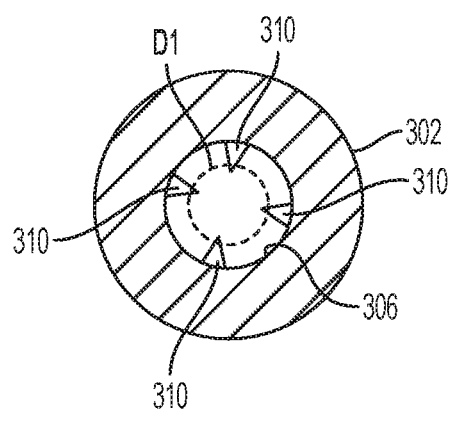
FIG. 3 is a top down view of an embodiment of a trocar simulation device for receiving a shaft of the surgical tool of FIG. 1.

The tool holder can minimize shaft bending loads, resist shaft movement, and provide centering of the shaft of a surgical tool through a variety of different approaches and by using a variety of different engagement features. In one embodiment illustrated in FIG. 3, the tool holder 302 has a plurality of crush ribs 310 disposed therein. The crush ribs 310 are spaced radially around an inner perimeter of the tool holder 302 such that they engage a circumference of a tool inserted therethrough. The crush ribs 310 can be made of a variety of deformable and/or elastic materials, such as plastic or metal. For example, the crush ribs 310 can be made of a plastic insert on a metallic ring, or the crush ribs 310 can be entirely plastic. The crush ribs can have various shapes and sizes, such as triangular as shown. Alternative configurations include, for example, circular, oblong, square, etc. The crush ribs 310 extend into an opening 306 of the tool holder 302 through which a shaft of a surgical tool, such as the shaft 122 of the surgical tool 110, is inserted. As the shaft 122 is inserted through the opening 306, the crush ribs 310 are configured to resist deformation. As represented by a dotted line D1 in FIG. 3, a diameter of the shaft 122 is smaller than the opening 306 but large enough to contact all of the crush ribs 310. When the shaft 122 overcomes the resistance of the crush ribs 310, the crush ribs 310 deform to allow the shaft 122 to be inserted into the opening 306 while maintaining contact with the shaft 122 and resisting further deformation, consequently resisting bending or tilting of the shaft 122 during use. Because there is a plurality of crush ribs 310 around the opening 306, the crush ribs 310 also maintain corresponding force around the diameter of the shaft 122 to maintain the shaft 122 aligned in a longitudinal center of the opening 306.

Figure 4:
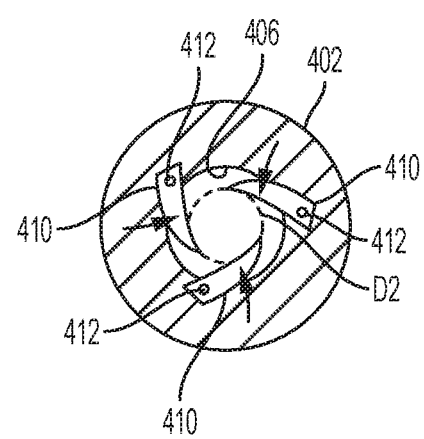
FIG. 4 is a top down view of another embodiment of a trocar simulation device for receiving the shaft of the surgical tool of FIG. 1.

FIG. 4 illustrates another embodiment of a tool holder 402 with spring-loaded arms 410 disposed therein. The spring-loaded arms 410 are pivotably mounted about a pivot point 412 and extend into an opening 406 of the tool holder 402 through which a shaft of a surgical tool, such as the shaft 122 of the surgical tool 110, is inserted. The spring-loaded arms 410 are biased toward a longitudinal center of the opening 406, and as the shaft 122 is inserted through the opening 406, the spring-loaded arms 410 resist pivotal movement away from the opening 406. As represented by a dotted line D2 in FIG. 4, a diameter of the shaft 122 is smaller than the opening 406 but large enough to contact all of the spring-loaded arms 410. When the shaft 122 overcomes the spring bias of the spring-loaded arms 410, the spring-loaded arms 410 pivot about the pivot points 412 to allow the shaft 122 to be inserted into the opening 406 while maintaining contact with the shaft 122 and resisting further pivoting, consequently resisting bending or tilting of the shaft 122. Because there is a plurality of spring-loaded arms 410 around the opening 406, the spring-loaded arms 410 maintain corresponding force around the diameter of the shaft 122 to maintain the shaft 122 aligned in the longitudinal center of the opening 406. The spring-loaded arms 410 can be made of a variety of materials, such as plastic or metal, and can have various shapes and sizes, such as triangles, oblongs, squares, etc. The arms 410 can pivot into recesses formed in the interior wall of the tool holder 402 as they are forced to pivot from insertion of an elongate shaft so that enough of each arm 410 extends into the opening 406 to support the elongate shaft while any extra portion of the arm 410 that is not required to extend into the opening to contact and support the shaft will be pivoted into the recess. This amount will vary depending on a diameter of the shaft.

Figure 5:
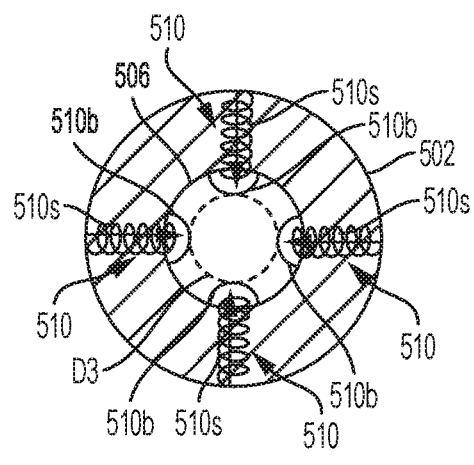
FIG. 5 is a top down view of another embodiment of a trocar simulation device for receiving the shaft of the surgical tool of FIG. 1.

FIG. 5 illustrates another embodiment of a tool holder 502 with a plurality of spring-biased centering balls 510 disposed therein. The spring-biased centering balls 510 each have a spring 510s that biases a ball 510b toward a center of an opening 506 of the tool holder 502 through which a shaft of a surgical tool, such as the shaft 122 of the surgical tool 110, is inserted. The springs 510s bias the balls 510b toward a longitudinal center of the opening 406 so that, as the shaft 122 is inserted through the opening 506, the springs 510s cause the balls 510b to resist moving away from the longitudinal center. Because there are a plurality of spring-biased centering balls 510 around the opening 506, the spring-biased centering balls 510 maintain corresponding force around the diameter of the shaft 122 to maintain the shaft 122 aligned in the longitudinal center of the opening 506. As represented by a dotted line D3 in FIG. 5, a diameter of the shaft 122 is smaller than the opening 506 but large enough to contact all of the balls 510b of the spring-biased centering balls 510. When the shaft 122 overcomes the spring bias of the springs 510s, the balls 510b are compressed out of the opening 506 just enough to allow the shaft 122 to be inserted into the opening 506 while maintaining contact with the shaft 122 and resisting further compression, consequently resisting bending or tilting of the shaft 122.

Each spring-biased centering ball 510 can be in a cavity in the holder 502 so that the ball 510b can move in and out of the cavity as larger or smaller shafts are inserted through the holder 502. Each ball 510b is mated to its corresponding spring 510s so that the balls 510b do not decouple from the spring 510s or the holder 502. However, other techniques can be used to retain the balls within the cavities. The spring-biased centering balls 510 can be made of a variety of materials, such as plastic or metal. Instead of springs, the balls can be coupled to other compressible materials that provide the same compressible and adjustable functionality to the balls.

Figure 6:
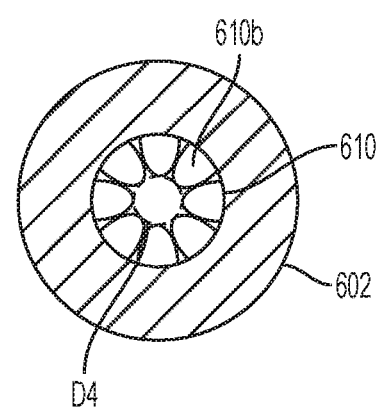
FIG. 6 is a top down view of another embodiment of a trocar simulation device for receiving the shaft of the surgical tool of FIG. 1.

FIG. 6 illustrates another embodiment of a tool holder 602 with a semi-segmented balloon 610 disposed therein. The balloon 610 has a plurality of semi-segmented bulbous bumps 610b that are filled with an inflation fluid, such as air or saline. The bumps extends into a center of an opening 606 of the tool holder 602 through which a shaft of a surgical tool, such as the shaft 122 of the surgical tool 110, is inserted. The bulbous bumps 610b create a narrow passageway in a longitudinal center of the opening 606 so that, as the shaft 122 is inserted through the opening 606, the bumps 610b resist moving out of the opening 606. As represented by a dotted line D4 in FIG. 6, a diameter of the shaft 122 is smaller than the opening 606 but large enough to contact all of the bumps 610b. As the shaft 122 is inserted into the opening 606, the shaft 122 forces the bumps 610b to compress partially out of the opening 606 just enough to allow the shaft 122 to be inserted into the opening 606 while maintaining contact with the shaft 122 and resisting further compression, consequently resisting bending or tilting of the shaft 122. Because there is a plurality of bumps 610b around the opening 606, the bumps 610b maintain corresponding force around the diameter of the shaft 122 to maintain the shaft 122 aligned in the longitudinal center of the opening 606. The semi-segmented balloon 610 can be made of a variety of materials, such as plastic. The semi-segmented balloon 610 can be inflated through use of an insufflation mechanism designed to be used by a trocar in a surgical system to which the tool holder 602 is attached.

Figure 7:
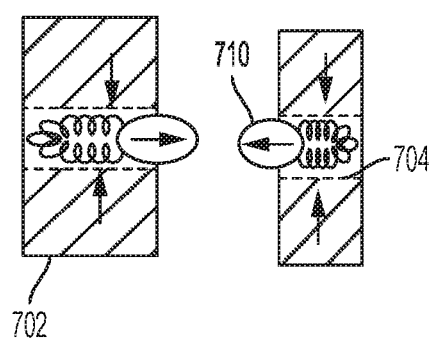
FIG. 7 is a cross-sectional side view of another embodiment of a trocar simulation device for receiving the shaft of the surgical tool of FIG. 1.
Figure 8:
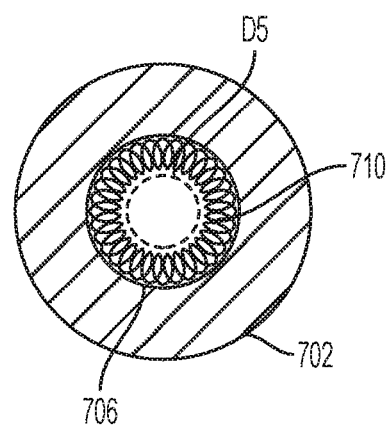
FIG. 8 is a top down view of the trocar simulation device of FIG. 7 for receiving the shaft of the surgical tool of FIG. 1.

Another embodiment of a tool holder 702 is illustrated in FIGS. 7 and 8. The tool holder 702 has an elastomeric material 710 disposed in a channel 704 formed within the body of the tool holder. The elastomeric material 710 extends into a center of an opening 706 of the tool holder 702 through which a shaft of a surgical tool, such as the shaft 122 of the surgical tool 110, is inserted. The elastomeric material 710 creates a narrow passageway in a longitudinal center of the opening 706 so that, as the shaft 122 is inserted through the opening 706, the elastomeric material 710 resists moving out of the opening 706. As represented by a dotted line D5 in FIG. 8, a diameter of the shaft 122 is smaller than the opening 706 but large enough to contact the elastomeric material 710. As the shaft 122 is inserted into the opening 706, the shaft 122 compresses the elastomeric material 710 partially out of the opening 706 enough to allow the shaft 122 to be inserted through the opening 706 while the elastomeric material 710 maintains contact with the shaft 122 and resists further compression, consequently resisting bending or tilting of the shaft 122. The elastomeric material 710 maintains force around the entire diameter of the shaft 122 to maintain the shaft 122 aligned in the longitudinal center of the opening 706. The elastomeric material 710 can be made of a variety of materials, such as Silicone, Nitrile, Ethylene Propylene Diene Monomer (EPDM), Fluoroelastomer (FKM), Neoprene, etc.

The engagement features providing support to a tool shaft discussed above can be locked into place to provide a fixed amount of support to the tool shaft, for example by using levers and/or ratchets to lock the spring-loaded arms 410 or the spring-biased centering balls 510 into a fixed position. A diameter of the opening can also be adjustable, for example due to the ability of the engagement feature to move, flex, bend, compress, etc., and/or due to active adjustment of the diameter by, for example, adding or removing an inflation fluid or adjusting a position of the engagement features such as the arms or balls with a knob, lever, adjustment mechanism, etc. The tool holders can thus be used with a variety of tools that having varying shaft diameters, such as a device that is 12 mm at a distal end but only 8 mm mid-shaft, thus requiring a dynamic adjustment to maintain support on the shaft, or when using a smaller tool in a larger tool holder generally, such as an 8 mm tool in a 12 mm tool holder.

As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

The systems, devices, and methods disclosed herein can be implemented using one or more computer systems, which may also be referred to herein as digital data processing systems and programmable systems.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical method, comprising:
inserting an elongate shaft of a surgical tool into an opening of a tool holder mount on a distal end of a surgical robotic arm, the tool holder mount comprising a monolithic ring-shaped tool holder having a fixed outer diameter, and at least one inner biasing member on an interior surface of the tool holder, the tool holder mount being positioned adjacent to a tissue surface without extending into tissue, the opening dynamically adapting in size via the at least one inner biasing member to have an inner diameter that substantially corresponds to an outer diameter of the elongate shaft such that the tool holder mount resists angular forces applied to the elongate shaft to minimize a bending load applied to the shaft.

2. The method of claim 1, wherein the at least one inner biasing member is configured to bias the elongate shaft toward a center of the opening to resist angular forces applied to the elongate shaft.

3. The method of claim 2, wherein the at least one inner biasing member is selected from the group consisting of ribs, spring-biased centering balls, spring-biased arms, semi-segmented balloons, an elastomeric squeeze fit material, and combinations thereof.

4. The method of claim 1, wherein the at least one biasing member comprises a plurality of spring-biased members that are biased toward a central axis of the opening to adjust a size of the inner diameter of the opening.

5. The method of claim 1, wherein the at least one inner biasing member is configured to move radially to adjust a size of the inner diameter of the opening.

6. The method of claim 1, wherein a distal end of a carrier arm coupled to the distal end of the surgical robotic arm has the tool holder mount mounted thereon, and a housing of the surgical tool is movably coupled to a tool driver mounted on a proximal portion of the carrier arm.

7. A surgical method, comprising:
inserting an elongate shaft of a surgical tool into an opening of a tool holder mount on a distal end of a surgical robotic arm, the tool holder mount comprising a monolithic ring-shaped tool holder having a fixed outer diameter, an inner portion configured to provide force on the elongate shaft along at least two axes, and a tool driver, the tool holder mount being positioned adjacent to a tissue surface without extending into tissue, the opening dynamically adapting in size via the inner portion to have an inner diameter that substantially corresponds to an outer diameter of the elongate shaft such that the tool holder mount resists angular forces applied to the elongate shaft; and
releasably coupling the surgical tool to the tool driver located on the distal end of the surgical arm.

8. The surgical method of claim 7, wherein the inner portion is selected from the group consisting of ribs, spring-biased centering balls, spring-biased arms, semi-segmented balloons, an elastomeric squeeze fit material, and combinations thereof.

9. The surgical method of claim 7, wherein the inner portion generates angular force to minimize a bending load on the surgical tool.

10. The surgical method of claim 9 further wherein the inner portion comprises a plurality of evenly spaced members configured to center the surgical tool inserted therein.

* * * * *